US011963662B2

(12) United States Patent
Takeuchi et al.

(10) Patent No.: US 11,963,662 B2
(45) Date of Patent: Apr. 23, 2024

(54) CHANNEL UNIT FOR ENDOSCOPE AND ENDOSCOPE

(71) Applicant: OLYMPUS CORPORATION, Tokyo (JP)

(72) Inventors: Hiromi Takeuchi, Koganei (JP); Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 290 days.

(21) Appl. No.: 17/343,295

(22) Filed: Jun. 9, 2021

(65) Prior Publication Data

US 2021/0290045 A1   Sep. 23, 2021

Related U.S. Application Data

(63) Continuation of application No. PCT/JP2018/045685, filed on Dec. 12, 2018.

(51) Int. Cl.
*A61B 1/00* (2006.01)
*A61B 1/005* (2006.01)
*A61B 1/018* (2006.01)

(52) U.S. Cl.
CPC ............ *A61B 1/0014* (2013.01); *A61B 1/005* (2013.01); *A61B 1/018* (2013.01)

(58) Field of Classification Search
CPC ... A61B 1/0014; A61B 1/018; A61B 1/00101; A61B 1/00137
USPC ........................................................ 600/104
See application file for complete search history.

(56) References Cited

U.S. PATENT DOCUMENTS

| 6,071,233 | A | 6/2000 | Ishikawa et al. |
| 2005/0234297 | A1 | 10/2005 | Devierre et al. |
| 2006/0079735 | A1 | 4/2006 | Martone et al. |
| 2008/0177135 | A1* | 7/2008 | Muyari ............. A61B 1/00087 600/104 |
| 2008/0275483 | A1* | 11/2008 | Makower ............... A61B 10/06 600/114 |
| 2013/0317515 | A1* | 11/2013 | Kuroda .............. A61B 17/3478 606/113 |

(Continued)

FOREIGN PATENT DOCUMENTS

| JP | 05-307143 A | 11/1993 |
| JP | 11-192203 A | 7/1999 |

(Continued)

OTHER PUBLICATIONS

International Search Report dated Feb. 12, 2019 received in PCT/JP2018/045685.

*Primary Examiner* — John P Leubecker
*Assistant Examiner* — Li-Ting Song
(74) *Attorney, Agent, or Firm* — Scully, Scott, Murphy & Presser, P.C.

(57) ABSTRACT

A channel unit for an endoscope includes a conduit, a mounting member and a connection member having one end connected to the mounting member and another end connected to a distal end of the conduit, the connection member having flexibility and a variable length in a longitudinal direction, and a proximal end side fixing portion of the connection member is movable back and forth in the longitudinal direction with respect to a distal end side fixing portion of the connection member as the conduit moves back and forth in the longitudinal direction.

18 Claims, 16 Drawing Sheets

(56) References Cited

U.S. PATENT DOCUMENTS

| | | | |
|---|---|---|---|
| 2014/0343358 A1* | 11/2014 | Hameed | G02B 23/2423 |
| | | | 600/109 |
| 2016/0029875 A1 | 2/2016 | Okada | |
| 2017/0049302 A1* | 2/2017 | Isoda | A61B 1/00098 |
| 2017/0100017 A1* | 4/2017 | Terliuc | A61B 1/018 |
| 2020/0046201 A1* | 2/2020 | Ho | A61B 1/00135 |
| 2021/0169309 A1* | 6/2021 | Matsuoka | A61B 1/00087 |
| 2021/0338046 A1* | 11/2021 | Yahagi | A61B 17/00234 |

FOREIGN PATENT DOCUMENTS

| | | |
|---|---|---|
| JP | 2003-210399 A | 7/2003 |
| JP | 2005-131211 A | 5/2005 |
| JP | 2007-532262 A | 11/2007 |
| JP | 2012-024597 A | 2/2012 |
| JP | 2012-161454 A | 8/2012 |
| WO | 03/057019 A1 | 7/2003 |
| WO | 2014/199759 A1 | 12/2014 |

* cited by examiner

CHANNEL UNIT FOR ENDOSCOPE AND ENDOSCOPE

CROSS REFERENCE TO RELATED APPLICATION

This application is a continuation application of PCT/JP2018/045685 filed on Dec. 12, 2018, the entire contents of which are incorporated herein by this reference.

BACKGROUND OF THE INVENTION

1. Field of the Invention

The present invention relates to a channel unit for an endoscope provided with a conduit, at least part of which is located in a longitudinal direction of an endoscope insertion portion on an outer circumferential surface of the endoscope insertion portion, and the endoscope.

2. Description of the Related Art

In recent years, endoscopes have been widely used in medical and industrial fields.

Endoscopes used in the medical field can observe an organ in a body cavity by inserting an elongated insertion portion into a body cavity, which is a subject or can conduct various treatments using a treatment instrument inserted into an insertion channel for the treatment instrument provided for the endoscope if necessary.

On the other hand, endoscopes used in the industrial field can observe scars and corrosion or the like at a site to be examined in an object by inserting an elongated insertion portion of the endoscope into the object such as a jet engine or a pipe in a plant and perform inspections of various treatments. Note that the endoscopes used in the industrial field can also perform various treatments using a treatment instrument inserted into the aforementioned insertion channel if necessary.

Here, a configuration is well known in which an external channel, which is a conduit of a channel unit for an endoscope, can be attached or detached in a longitudinal direction of the insertion portion (hereinafter simply referred to as a "longitudinal direction") on an outer circumferential surface of the insertion portion.

A treatment instrument, which is different from the treatment instrument to be inserted into the insertion channel provided for the endoscope or an object to be inserted such as an insertion portion of another endoscope or the like can be inserted or removed into/from the external channel.

In this way, when, for example, the site to be examined is grasped by grasping forceps that are inserted into the external channel and protrude from a distal end opening of the external channel, the site to be examined can be subjected to a resection treatment using a resection instrument that protrudes from the distal end opening of the insertion channel inserted into the insertion channel of the endoscope.

Moreover, when the site to be examined is held by a treatment instrument for holding that is inserted into the insertion channel of the endoscope and protrudes from the distal end opening of the insertion channel, the insertion portion of the other endoscope that protrudes from the distal end opening of the external channel can be inserted into the opening of the site to be examined.

The external channel is fixed and locked to an outer circumferential surface of the insertion portion by a mounting member and a plurality of locking members so that the distal end opening is defined to be located at substantially the same position as the distal end face of the distal end portion of the insertion portion in the longitudinal direction.

More specifically, the external channel is located substantially parallel to the longitudinal direction along the outer circumferential surface of the insertion portion with at least part of the external channel brought close to the outer circumferential surface by the mounting member fixed to the outer circumference of the distal end portion of the insertion portion or a plurality of locking members locked at a set interval to the outer circumference closer to the proximal end side in the longitudinal direction than the bending portion of the insertion portion.

In this way, the treatment instrument (including the other endoscope) that protrudes from the distal end opening of the external channel is projected ahead of the distal end face of the distal end portion in the longitudinal direction substantially parallel to the longitudinal direction.

SUMMARY OF THE INVENTION

In order to attain the above described object, a channel unit for an endoscope according to an aspect of the present invention includes a conduit, at least part of which is located in a longitudinal direction of an endoscope insertion portion with respect to an outer circumferential surface of the endoscope insertion portion, a mounting member fixed to a distal end side of the endoscope insertion portion in the longitudinal direction, and a connection member having one end connected to the mounting member and another end connected to a distal end of the conduit in the longitudinal direction, the connection member having flexibility and a variable length in the longitudinal direction, in which a proximal end side fixing portion of the connection member to the conduit is movable back and forth in the longitudinal direction with respect to a distal end side fixing portion to the mounting member of the connection member as the conduit moves back and forth in the longitudinal direction.

An endoscope according to an aspect of the present invention is provided with a channel unit for an endoscope, the channel unit including a conduit, at least part of which is located in a longitudinal direction of an endoscope insertion portion with respect to an outer circumferential surface of the endoscope insertion portion, a mounting member fixed to a distal end side of the endoscope insertion portion in the longitudinal direction, and a connection member having one end connected to the mounting member and another end connected to a distal end of the conduit in the longitudinal direction, the connection member having flexibility and a variable length in the longitudinal direction, in which a proximal end side fixing portion of the connection member to the conduit is movable back and forth in the longitudinal direction with respect to a distal end side fixing portion to the mounting member of the connection member as the conduit moves back and forth in the longitudinal direction.

DETAILED DESCRIPTION OF THE PREFERRED EMBODIMENTS

Hereinafter, embodiments of the present invention will be described with reference to the accompanying drawings.

First Embodiment

Figure 1:
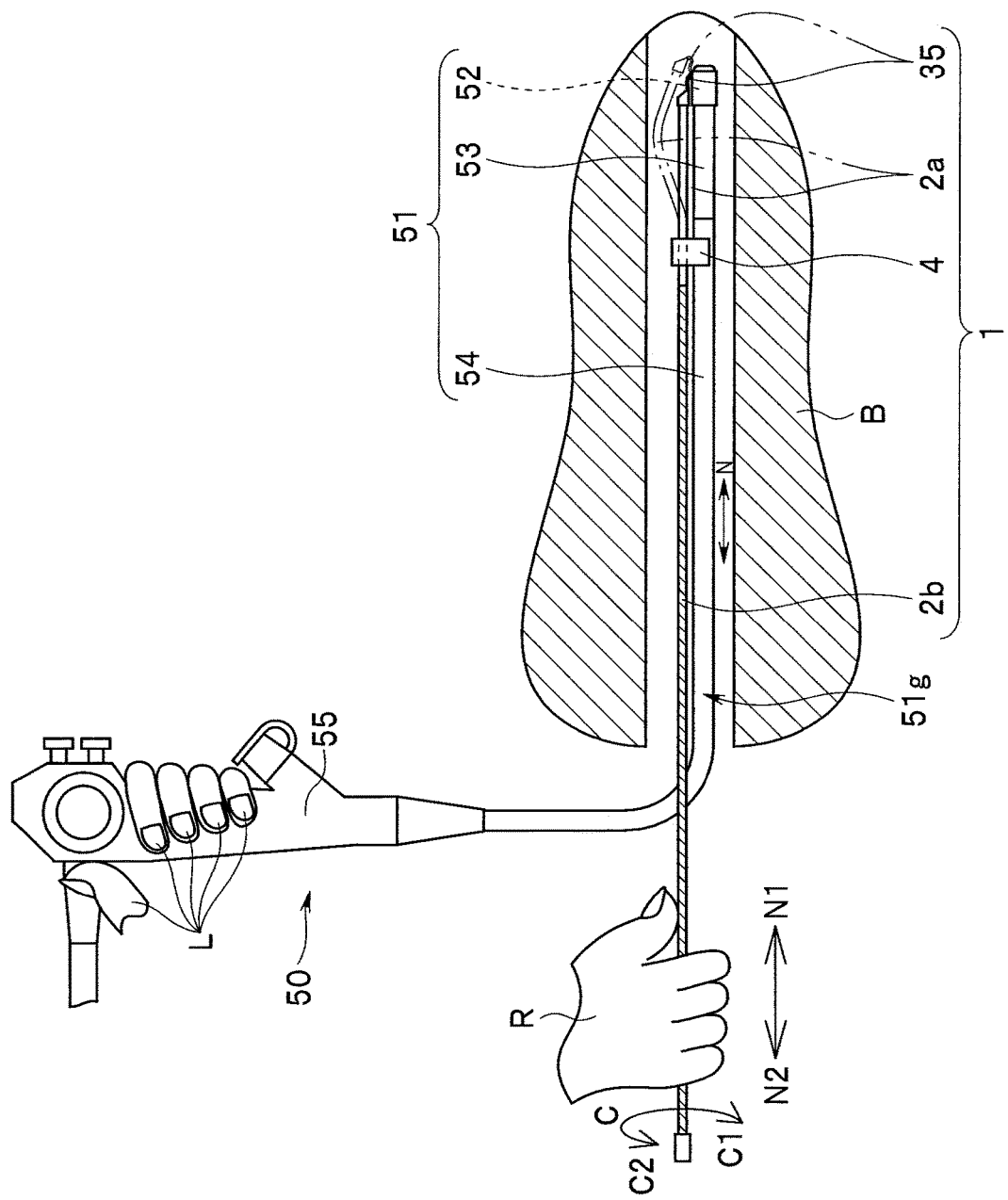
FIG. 1 is a diagram schematically illustrating a state in which an insertion portion of an endoscope to which a channel unit for an endoscope according to a first embodiment is attached is inserted in a subject.
Figure 2:
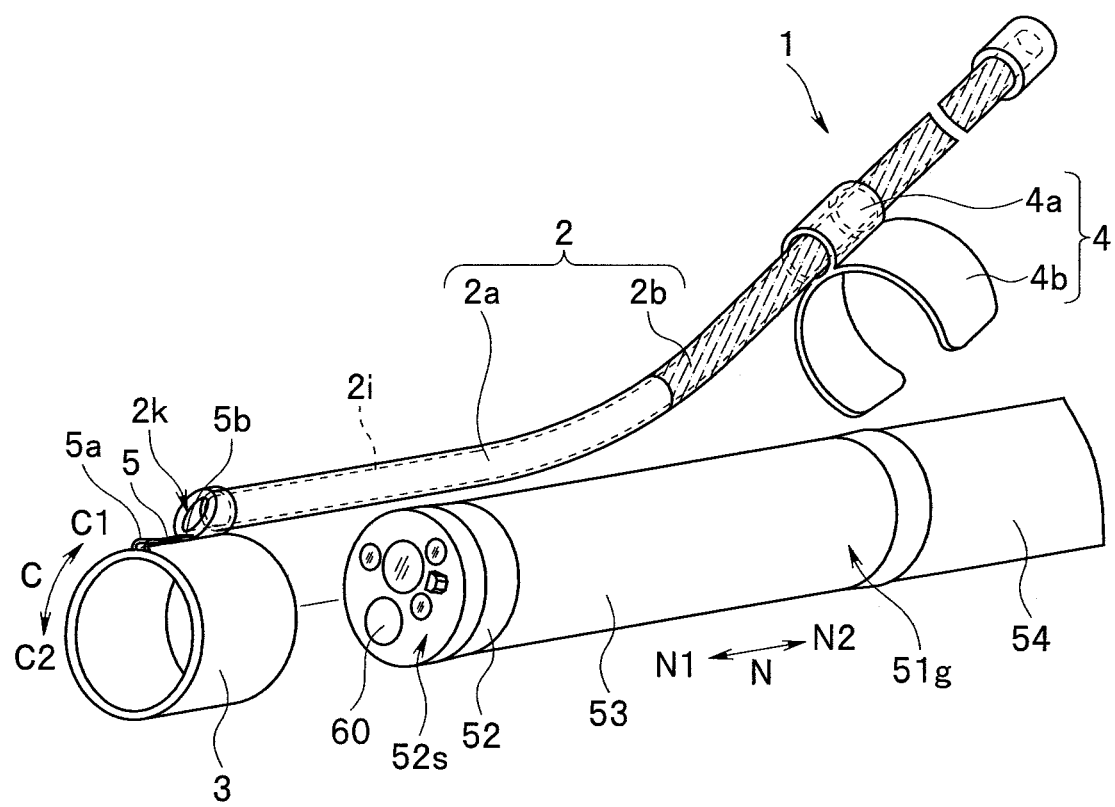
FIG. 2 is a partial perspective view illustrating a state in which the channel unit for an endoscope is removed from the distal end side of the insertion portion of the endoscope in FIG. 1.

FIG. 1 is a diagram schematically illustrating a state in which an insertion portion of an endoscope to which a channel unit for an endoscope according to the present embodiment is attached is inserted in a subject and FIG. 2 is a partial perspective view illustrating a state in which the channel unit for an endoscope is removed from the distal end side of the insertion portion of the endoscope in FIG. 1.

Figure 3:
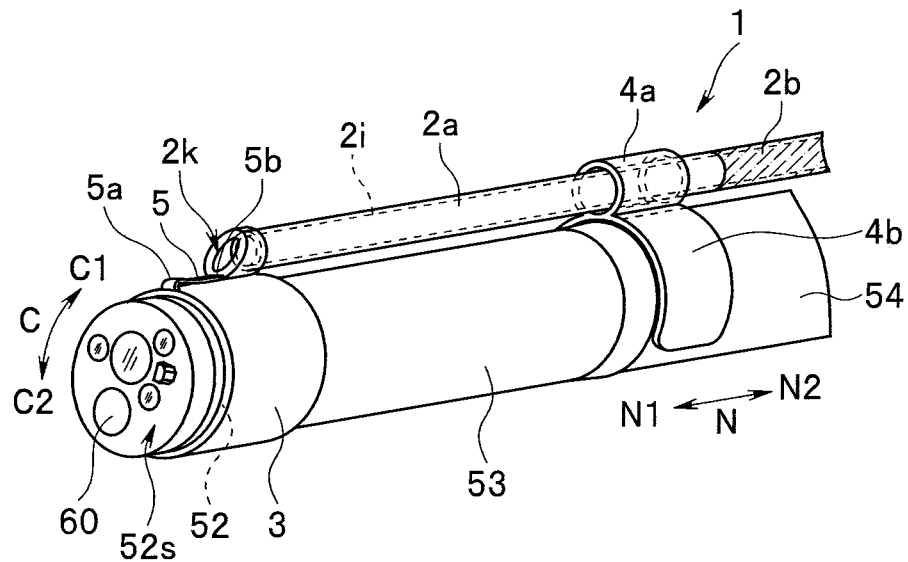
FIG. 3 is a partial perspective view illustrating a state in which the channel unit for an endoscope in FIG. 2 is attached to the distal end side of the insertion portion of the endoscope.
Figure 4:
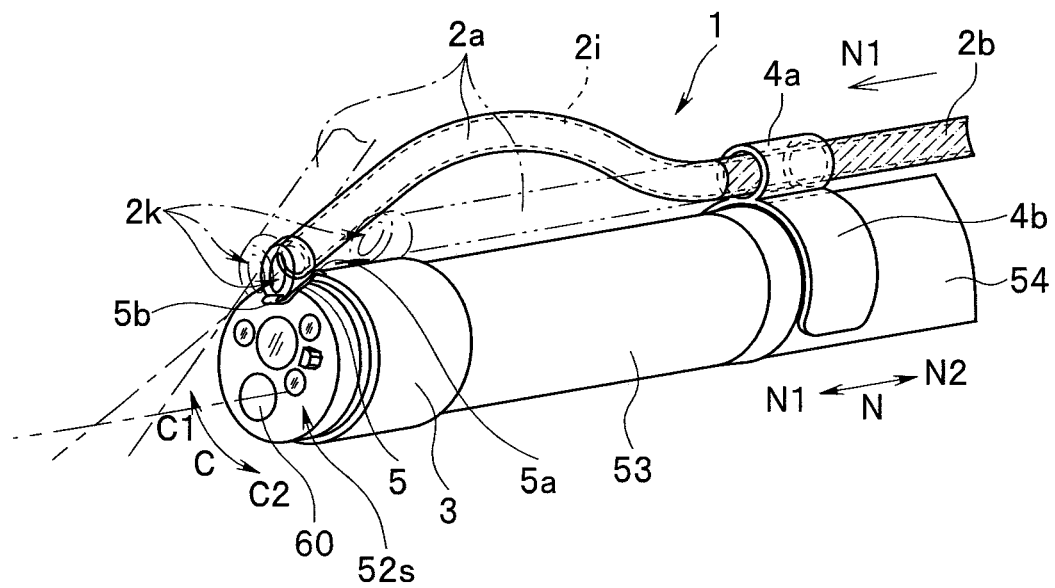
FIG. 4 is a partial perspective view illustrating a state in which an external channel of the channel unit for an endoscope in FIG. 3 is pushed forward and the direction of a distal end opening of the external channel is displaced in the longitudinal direction.

FIG. 3 is a partial perspective view illustrating a state in which the channel unit for an endoscope in FIG. 2 is attached to the distal end side of the insertion portion of the endoscope and FIG. 4 is a partial perspective view illustrating a state in which the external channel of the channel unit for an endoscope in FIG. 3 is pushed forward and the direction of the distal end opening of the external channel is displaced in the longitudinal direction.

Figure 5:
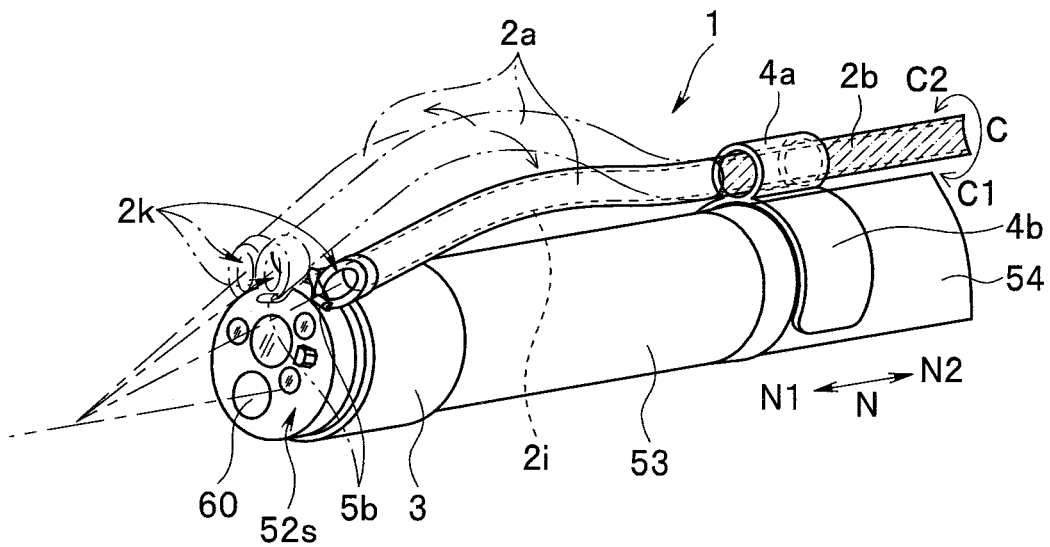
FIG. 5 is a partial perspective view illustrating a state in which the external channel of the channel unit for an endoscope in FIG. 3 is twisted and the direction of the distal end opening of the external channel is displaced in a direction substantially orthogonal to the longitudinal direction.
Figure 6:
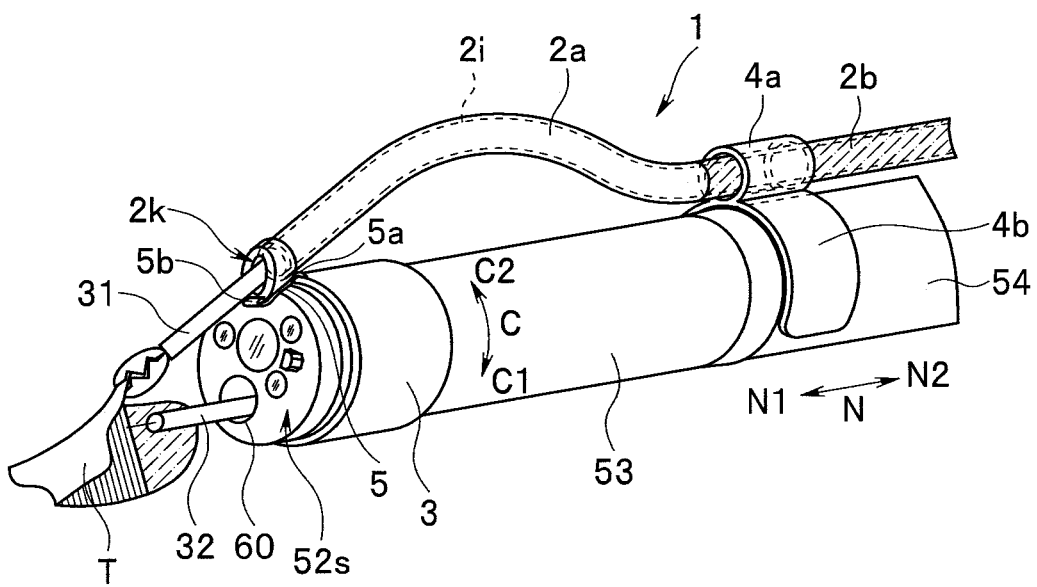
FIG. 6 is a partial perspective view illustrating a state in which a lesion region is grasped by grasping forceps that protrude from the distal end opening of the external channel in FIG. 4 and the lesion region is resected by a resection instrument that protrudes from the insertion channel of the endoscope.

Furthermore, FIG. 5 is a partial perspective view illustrating a state in which the external channel of the channel unit for an endoscope in FIG. 3 is twisted and the direction of the distal end opening of the external channel is displaced in a direction substantially orthogonal to the longitudinal direction and FIG. 6 is a partial perspective view illustrating a state in which a lesion region is grasped by grasping forceps that protrude from the distal end opening of the external channel in FIG. 4 and the lesion region is resected by a resection instrument that protrudes from the insertion channel of the endoscope.

As illustrated in FIG. 1, a channel unit 1 for an endoscope is attached to an insertion portion 51, which is elongated in a longitudinal direction N of an endoscope 50 and inserted into a subject B together with the insertion portion 51.

To give an example, when an operation portion 55 of the endoscope 50 is grasped by a left hand L of an operator, the insertion portion 51 grasped by a right hand R of the operator is inserted into the subject B with the external channel unit 1 for an endoscope attached to the insertion portion 51.

Then, with the external channel unit 1 for an endoscope, the operator grasps an external channel 2, which will be described later, by the right hand R and performs various operations such as an advancing/retreating operation in a longitudinal direction N or a twisting operation in a circumferential direction C on the external channel 2 by the right hand R.

As illustrated in FIG. 1 and FIG. 2, the channel unit 1 for an endoscope mainly includes an external channel 2, which is a conduit, a mounting member 3, a locking member 4 and a connection member 5. Note that the external channel 2, the mounting member 3 and the connection member 5 may be formed integrally.

The external channel 2 is made of a flexible member, formed in a cylindrical shape having a predetermined length in the longitudinal direction N and at least part of the external channel 2 is located in the longitudinal direction N on an outer circumferential surface 51g of the insertion portion 51.

An insertion path 2i is formed inside the external channel 2, where various treatment instruments and an insertion portion 251 or the like (see FIG. 24) of another endoscope, which is different from the endoscope 50, are inserted.

Note that a distal end opening 2k of the insertion path 2i is formed at a distal end of the external channel 2 in the longitudinal direction N (hereinafter simply referred to as a "distal end").

Note that although FIG. 2 and later illustrate a case where the distal end opening 2k is formed into a shape inclined with respect to the longitudinal direction N, it goes without saying that the distal end opening 2k may also be formed in a shape substantially vertical to the longitudinal direction N.

In the present embodiment, the external channel 2 is formed such that a distal end side region 2a in the longitudinal direction N is more flexible than another region 2b, which is a region behind the distal end side region 2a.

For example, the distal end side region 2a is made of porous resin such as ePTFE and the other region 2b is made of non-porous resin such as PTFE, and so the distal end side region 2a is formed to be more flexible than the other region 2b. Note that members constituting the distal end side region 2a and the other region 2b are not limited to such members.

Regarding a length of the distal end side region 2a in the longitudinal direction N, as illustrated in FIG. 3, when the channel unit 1 for an endoscope is attached to the insertion portion 51 and the external channel 2 is in a non-operation state, the length of the distal end side region 2a is preferably set longer than a length of a bending portion 53 of the insertion portion 51.

The mounting member 3 is made of polysulfone, rubber or the like and formed into a cylindrical shape, attached to an outer circumferential surface of a distal end portion 52 connected to a distal end of the bending portion 53 of the insertion portion 51 and fixed by a frictional force or the like.

Note that the mounting member 3 is attached to the distal end portion 52 and then fixed to the distal end portion 52 by the frictional force of the mounting member 3 itself or the like so as not to move in the longitudinal direction N or in the circumferential direction C. The mounting member 3 can be attached/detached to/from the distal end portion 52.

The locking member 4 is composed of one or more components and is intended to lock the external channel 2 to the outer circumferential surface 51g of the insertion portion 51.

More specifically, the locking member 4 includes a cylindrical sliding portion 4a in which the external channel 2 slides back and forth in the longitudinal direction N, and a locking portion 4b, which is, for example, C-shaped, connected to the sliding portion 4a and locked to the outer circumferential surface 51g.

Note that a friction reducing member may be provided or a friction reducing process may be applied to an inner circumferential surface of the sliding portion 4a to improve slidability of the external channel 2.

The locking portion 4b causes the external channel 2 to be locked to the proximal end side of the bending portion 53 in the longitudinal direction N (hereinafter simply referred to as a "proximal end side"), that is, to an outer circumferential surface of a flexible tube portion 54 connected to a proximal end of the bending portion 53 in the longitudinal direction N (hereinafter simply referred to as a "proximal end").

In this way, as illustrated in FIG. 3, when the channel unit 1 for an endoscope is attached to the insertion portion 51, the external channel 2 is brought close to the outer circumferential surface 51g and located along the insertion portion 51.

Note that the locking portion 4b can be attached/detached to/from the outer circumferential surface 51g.

The connection member 5 is made of a flexible member.

Note that examples of the member constituting the connection member 5 include silicone rubber, fluorine rubber, string, silicone spring, plastic chain, metallic reticulated member.

One end of the connection member 5 is connected to the mounting member 3 and the other end of the connection member 5 is connected to the distal end of the external channel 2.

As illustrated in FIG. 4, the connection member 5 is configured such that the proximal end side fixing portion 5b to the external channel 2 can move back and forth in the longitudinal direction N with respect to the distal end side fixing portion 5a to the mounting member 3 along with advancing/retreating movement of the external channel 2 in the longitudinal direction N.

Furthermore, as illustrated in FIG. 5, since the connection member 5 is flexible, the connection member 5 is deformable in the circumferential direction C as the connection member 5 turns in the circumferential direction C caused by a twisting operation of the external channel 2.

Along with an operation of pushing the external channel 2 forward in the longitudinal direction N (hereinafter simply referred to as "forward"), when the proximal end side fixing portion 5b of the connection member 5 moves ahead of the distal end side fixing portion 5a as illustrated in FIG. 4, the connection member 5 tilts the direction of the distal end opening 2k of the external channel 2 in a plurality of directions in a three-dimensional space with respect to the longitudinal direction N along with subsequent advancing/retreating movement in the longitudinal direction N or turning operation in the circumferential direction C of the external channel 2 as illustrated in FIG. 4 or FIG. 5.

Note that since the rest of the configuration of the external channel for an endoscope is the same as the conventional configuration, description of the configuration will be omitted.

Next, operation of the present embodiment will be described.

As illustrated in FIG. 3, in a state in which the external channel unit 1 for an endoscope is attached to the insertion portion 51 and inserted in the subject B as illustrated in FIG. 1, when the operator performs an operation of pushing the external channel 2 forward first, the proximal end side fixing portion 5b moves ahead of the distal end side fixing portion 5a as described above.

After this, when the operator further performs an operation of pushing the external channel 2 forward, since the mounting member 3 is fixed to the distal end portion 52, forward movement of the external channel 2 equal to or greater than the length of the connection member 5 in the longitudinal direction N is restricted.

As a result, as illustrated in FIG. 4, the flexible distal end side region 2a of the external channel 2 is deformed arcuately. Along with this deformation, the position or direction of the distal end opening 2k can be changed in a plurality of directions in the three-dimensional space with respect to the longitudinal direction N including not only a direction orthogonal to the longitudinal direction N but also a front/back position of the longitudinal direction N.

Therefore, an angle or position of the treatment instrument that protrudes from the distal end opening 2k can also be changed to desired positions in a plurality of directions in the three-dimensional space.

In this state, when the operator performs a twisting operation on the external channel 2 in a direction C1 or C2 of the circumferential direction C, since the connection member 5 is made of a flexible member, the connection member 5 changes the direction of the distal end opening 2k to the same direction.

In this case, since the distal end side fixing portion 5a is fixed to the mounting member 3, movement of the external channel 2 in the circumferential direction C equal to or greater than a maximum deformable amount of the connection member 5 is restricted.

Therefore, the distal end side region 2a is freely deformed in the circumferential direction C. and the distal end opening 2k moves in the circumferential direction C as shown by from a two-dot dashed line to a solid line or from a two-dot dashed line to a one-dot dashed line in FIG. 5.

Note that the movement of the distal end side region 2a in the circumferential direction C may also be performed along a rail (not shown) formed on the outer circumferential surface of the mounting member 3.

As a result, the position or direction of the distal end opening 2k can be changed in a plurality of directions in the three-dimensional space including advancing/retreating movement in the aforementioned longitudinal direction N and inclination with respect to the longitudinal direction N.

Therefore, the angle or position of the treatment instrument that protrudes from the distal end opening 2k can also be changed to desired positions in the plurality of directions in the three-dimensional space.

This improves resecting performance with respect to a lesion region T in such a manner that, as illustrated in FIG. 6, along with deformation of the distal end side region 2a, when a grasping tool 31 inserted in the insertion path 2i is tilted with respect to the longitudinal direction N, the grasping tool 31 is caused to protrude forward from the distal end opening 2k, and the grasping tool 31 is caused to grasp a lesion region T and tension is added to the lesion region T in a direction different from the longitudinal direction N, it is possible to resect the lesion region T using a resection instrument 32 that protrudes forward from the insertion channel 60 of the endoscope 50, or other manners.

Thus, it has been shown in the present embodiment that the mounting member 3 fixed to the distal end portion 52 and the external channel 2 in the channel unit 1 for an endoscope are connected via the flexible connection member 5.

It has also been shown that the connection member 5 is configured such that the proximal end side fixing portion 5b is movable back and forth in the longitudinal direction N with respect to the distal end side fixing portion 5a along with the advancing/retreating movement of the external channel 2 in the longitudinal direction N.

In this way, since the connection member 5 is flexible and is made variable in the circumferential direction C, the connection member 5 causes the distal end side region 2a of the external channel 2 to be deformed by an amount corresponding to a length of the connection member 5 in the longitudinal direction N or by a maximum deformable amount of the connection member 5 in the circumferential direction C along with advancing/retreating movement of the external channel 2 in the longitudinal direction N or an operation of twisting the external channel 2 in the circumferential direction C.

As a result, it is possible to change the angle or position of the distal end opening 2k, that is, the angle or position of the treatment instrument that protrudes forward from the distal end opening 2k to desired positions in a plurality of directions in the three-dimensional space without changing an observation view.

Furthermore, since the connection member 5 is flexible, the connection member 5 is not bent by following the curvature of the bending portion 53 or does not follow the large advancing/retreating movement of the insertion portion 51 in the longitudinal direction N, the angle or position of the distal end opening 2k along with the movement of the insertion portion 51, that is, the angle or position of the treatment instrument that protrudes forward from the distal end opening 2k is hardly variable.

From the above, it is possible to provide the channel unit 1 for an endoscope and the endoscope 50 configured to be able to change the distal end opening 2k to desired positions or angles without changing an observation direction of the endoscope.

Note that modifications will be illustrated hereinafter.

Although a case has been described in the aforementioned embodiment where one external channel 2 is used, the number of external channels 2 is not limited to one, and it goes without saying that a configuration with a plurality of external channels 2 may also be adopted.

In this case, the plurality of external channels 2 are arranged on the outer circumferential surface 51g of the insertion portion 51 at different positions in the circumferential direction C by the mounting member 3, the locking member 4 and the connection member 5, and the plurality of external channels 2 are each connected to the one mounting member 3 via a plurality of separately provided connection members 5.

Hereinafter, another modification will be illustrated using FIG. 7 and FIG. 8.

Figure 7:
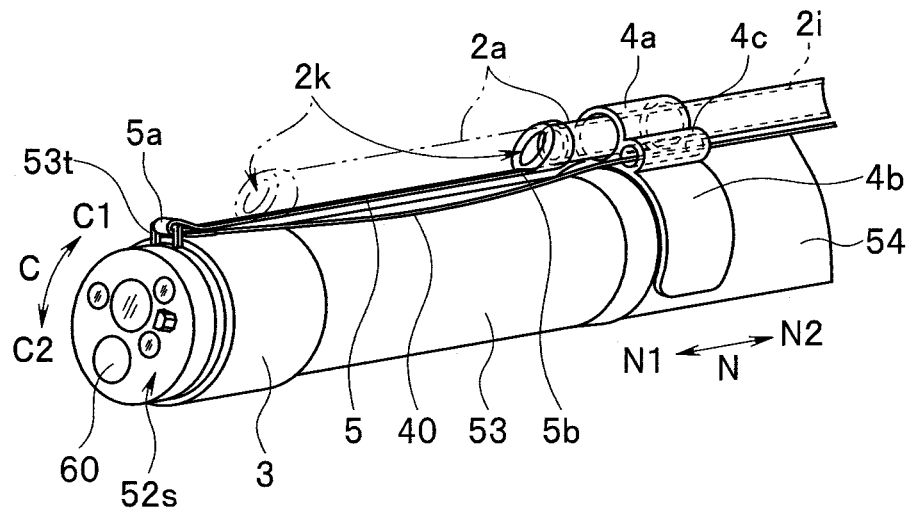
FIG. 7 is a partial perspective view illustrating a modification in which the connection member in FIG. 3 is made variable in the longitudinal direction.
Figure 8:
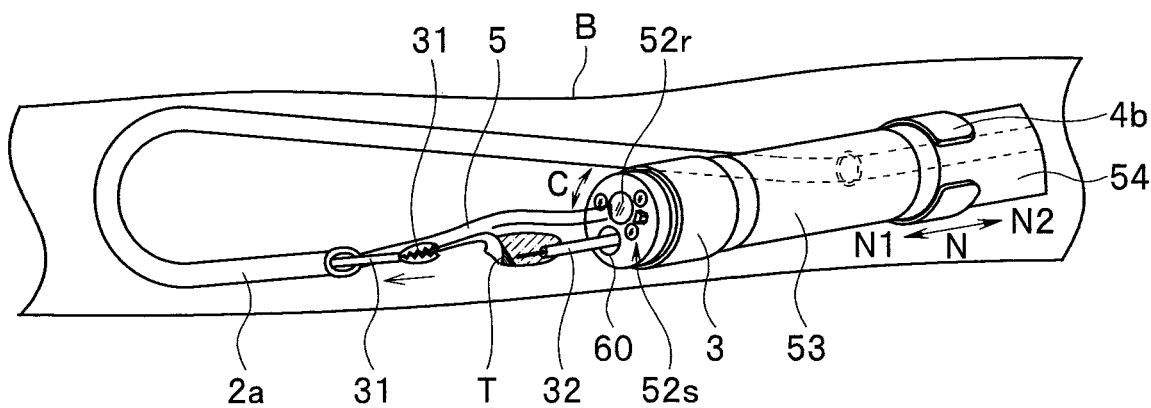
FIG. 8 is a partial perspective view illustrating a state in which the distal end opening of the external channel in FIG. 7 faces the distal end face of the insertion portion of the endoscope.

FIG. 7 is a partial perspective view illustrating a modification in which the connection member in FIG. 3 is made variable in the longitudinal direction and FIG. 8 is a partial perspective view illustrating a state in which the distal end opening of the external channel in FIG. 7 faces the distal end face of the insertion portion of the endoscope.

As illustrated in FIG. 7 and FIG. 8, the connection member 5 may be configured to be able to adjust the length in the longitudinal direction N in a variable manner.

More specifically, as illustrated in FIG. 7, in the present modification, the connection member 5 is formed to be longer in the longitudinal direction N than the connection member 5 in the aforementioned embodiment.

The distal end side fixing portion 5a is wound 180° around an arch-shaped hook 53t provided on the outer circumferential surface of the mounting member 3 and connected to a distal end of a length adjusting member 40.

The length adjusting member 40 has a length similar to the length of the external channel 2, is pushed/pulled back and forth in the longitudinal direction N by the operator, and is made of a flexible and strong member such as PTFE.

Note that the length adjusting member 40 is formed to have a smaller diameter than the diameter of the connection member 5 so as not to interfere with insertion when the insertion portion 51 to which the channel unit 1 for an endoscope is attached is inserted into the subject B.

Therefore, on one hand, when the length adjusting member 40 is pulled by the operator rearward in the longitudinal direction N (hereinafter simply referred to as "rearward"), the connected connection member 5 is wound 180° around the hook 53t, the connection member 5 thereby moves forward in the opposite direction to the pulling direction of the length adjusting member 40. The length of the connection member 5 is thereby reduced.

On the other hand, when the operator performs an operation of pulling the external channel 2 rearward in addition to an operation of pushing the length adjusting member 40 forward, since the connection member 5 connected to the length adjusting member 40 is wound 180° around the hook 53t, the connection member 5 moves rearward in the opposite direction to the pushing direction of the length adjusting member 40. The length of the connection member 5 is thereby increased.

In other words, the length adjusting member 40 makes the length of the connection member 5 in the longitudinal direction N variable.

According to such a configuration, when the length of the connection member 5 is set longer and the external channel 2 is pushed forward, the amount of deformation of the distal end side region 2a is greater in the longitudinal direction N and in the circumferential direction C than the amount of deformation in the aforementioned embodiment.

Note that, in this case, restriction of the length of forward protrusion of the proximal end side fixing portion 5b from the distal end side fixing portion 5a, that is, the length of the connection member 5 can be set by adding a small rearward pulling force to the length adjusting member 40. In other words, these lengths can be maintained.

Therefore, the length adjusting member 40 also serves as a restriction member to restrict the length of forward protrusion of the external channel 2 from the distal end side fixing portion 5a.

Thus, when the amount of deformation of the distal end side region 2a increases, for example, as illustrated in FIG. 8, after the proximal end side fixing portion 5b moves ahead of the distal end side fixing portion 5a along with the operation of pushing the external channel 2, the connection member 5 causes the distal end side region 2a to be deformed 1800 at a position ahead of the distal end face 52s of the distal end portion 52 in the subject B and can thereby cause the distal end opening 2k to face the distal end face 52s.

According to such a configuration, when the lesion region T is pulled forward and fixed using the grasping tool 31 which is caused to protrude from the distal end opening 2k, it is possible to perform an operation of resecting the lesion region T using the resection instrument 32 caused to protrude forward from the insertion channel 60.

In this case, since the grasping tool 31 is located ahead of the resection instrument 32, the grasping tool 31 never interferes when the operator resects the lesion region T using the resection instrument 32.

Furthermore, during resection of the lesion region T, even if dirt or the like adheres to an objective lens 52r provided on the distal end face 52s, it is possible to remove the dirt or the like adhering to the objective lens 52r using a protruding brush or the like instead of the grasping tool 31 from the distal end opening 2k without removing the insertion portion 51 from inside the subject B.

Note that in the present configuration, for example, in FIG. 8, since part of the connection member 5 is reflected in a view of the objective lens 52r, the connection member 5 is preferably made of a transparent member to prevent the observation view from deteriorating.

Note that the other effects are the same as the effects of the aforementioned embodiment.

Hereinafter, modifications of the configuration in which the length of the connection member 5 in the longitudinal direction N is made variable will be illustrated using FIG. 9 and FIG. 10.

Figure 9:
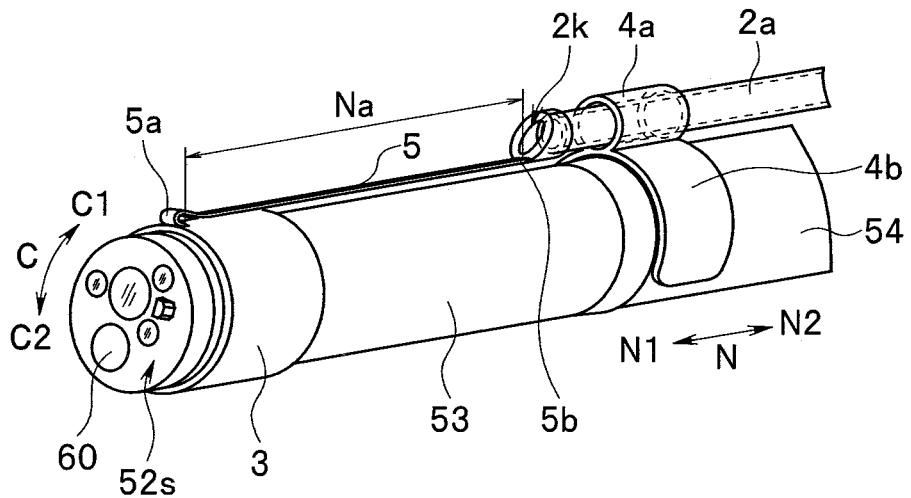
FIG. 9 is a partial perspective view illustrating a modification in which the connection member is formed to be longer in the longitudinal direction than the connection member in FIG. 3.
Figure 10:
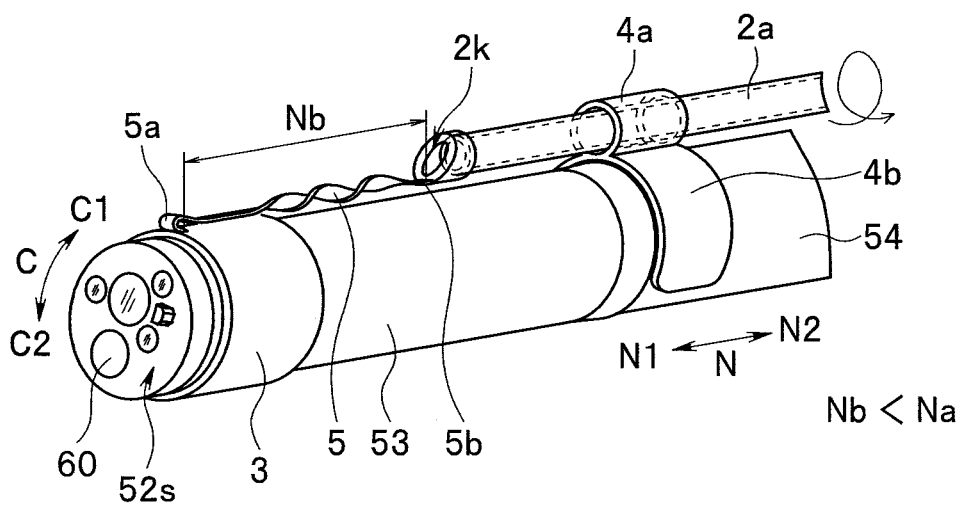
FIG. 10 is a partial perspective view illustrating a modification in which the connection member is made variable to be shorter in the longitudinal direction than the connection member in FIG. 9.

FIG. 9 is a partial perspective view illustrating a modification in which the connection member is formed to be longer in the longitudinal direction than the connection member in FIG. 3 and FIG. 10 is a partial perspective view illustrating a modification in which the connection member is made variable to be shorter in the longitudinal direction than the connection member in FIG. 9.

The configuration in which the length of the connection member 5 in the longitudinal direction N is made variable is not limited to the configuration illustrated in FIG. 7 and FIG. 8, and other configurations may be conceivable.

As illustrated, for example, in FIG. 9, by connecting the distal end side fixing portion 5a to the mounting member 3, connecting the proximal end side fixing portion 5b to the distal end of the external channel 2 and adding a twisting force in the circumferential direction C to the connection member 5 set to a first length Na longer than the length of the connection member 5 in FIG. 3 in the longitudinal direction N via the external channel 2, such a configuration may be adopted in which the length of the connection member 5 can be changed to a second length Nb (Nb<Na) shorter than the first length Na as illustrated in FIG. 10. Note that the second length Nb can be freely set by making a twisting amount of the external channel 2 variable.

Figure 11:
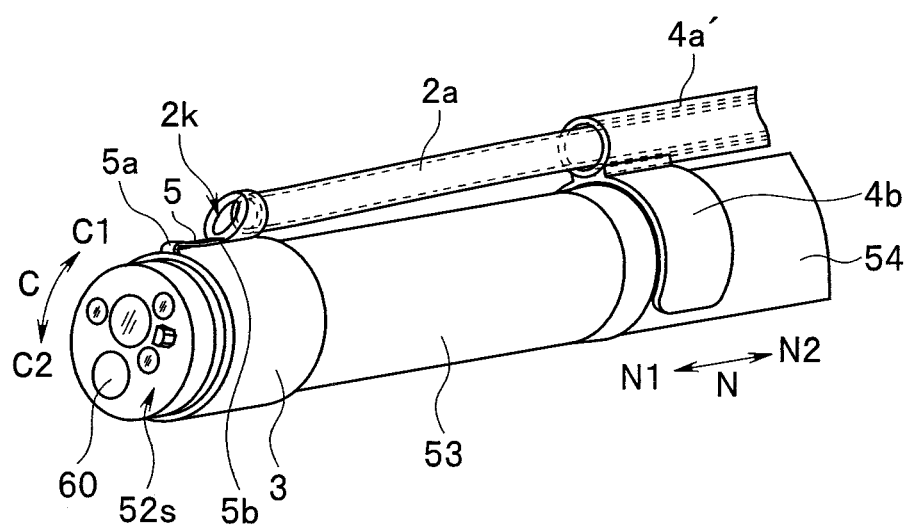
FIG. 11 is a partial perspective view illustrating a modification in which a sliding portion of the locking member in FIG. 3 is formed up to a proximal end of the external channel.

Furthermore, another modification will be illustrated using FIG. 11 hereinafter. FIG. 11 is a partial perspective view illustrating a modification in which the sliding portion of the locking member in FIG. 3 is formed up to a proximal end of the external channel.

It has been shown in the aforementioned embodiment that the distal end side region 2a in the external channel 2 is formed to be more flexible than the other region 2b.

Without being limited to this, the entire external channel 2 may be made of a flexible identical member and the outer circumference of the other region 2b except the distal end side region 2a may be covered with a rigid (more rigid than the external channel 2) sliding portion 4a' of the locking member 4.

Furthermore, in addition to the sliding portion 4a', the outer circumference of the other region 2b may be covered with a rigid tube.

With such a configuration, when the external channel 2 is pushed forward, the flexible distal end side region 2a not covered with the sliding portion 4a' or the rigid tube is deformed in the same way as in the aforementioned embodiment, and so effects similar to the effects in the aforementioned embodiment can be obtained.

Since it is not necessary to differentiate the hardness of the external channel 2 between the distal end side region 2a and the other region 2b, it is possible to reduce manufacturing cost.

Moreover, in the pushing operation or pulling operation of the external channel 2, since the external channel 2 moves back and forth in the longitudinal direction N, the external channel 2 may slide and directly contact the body wall of the subject B.

However, according to the present configuration, since the outer circumference of the other region 2b is covered with the sliding portion 4a' or the rigid tube, it is possible to prevent the external channel 2 from contacting the body wall of the subject B.

Figure 12:
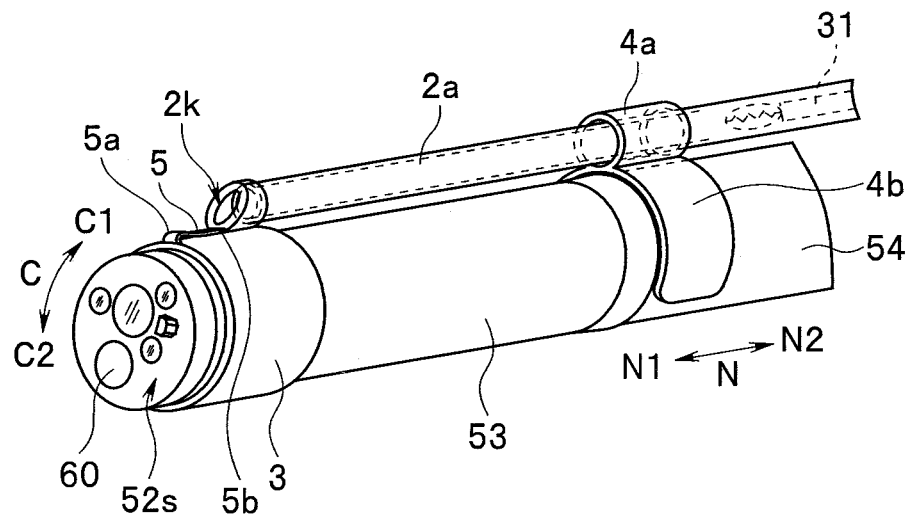
FIG. 12 is a partial perspective view illustrating a modification in which hardness of the other region of the external channel is increased using a treatment instrument inserted into the external channel in FIG. 3.

Hereinafter, a further modification will be illustrated using FIG. 12 and FIG. 13. FIG. 12 is a partial perspective view illustrating a modification in which hardness of the other region of the external channel is increased using a treatment instrument inserted into the external channel in FIG. 3 and FIG. 13 is a partial perspective view illustrating a state in which the external channel including a grasping tool is moved in the external channel in FIG. 12 ahead of the external channel in FIG. 12.

Figure 13:
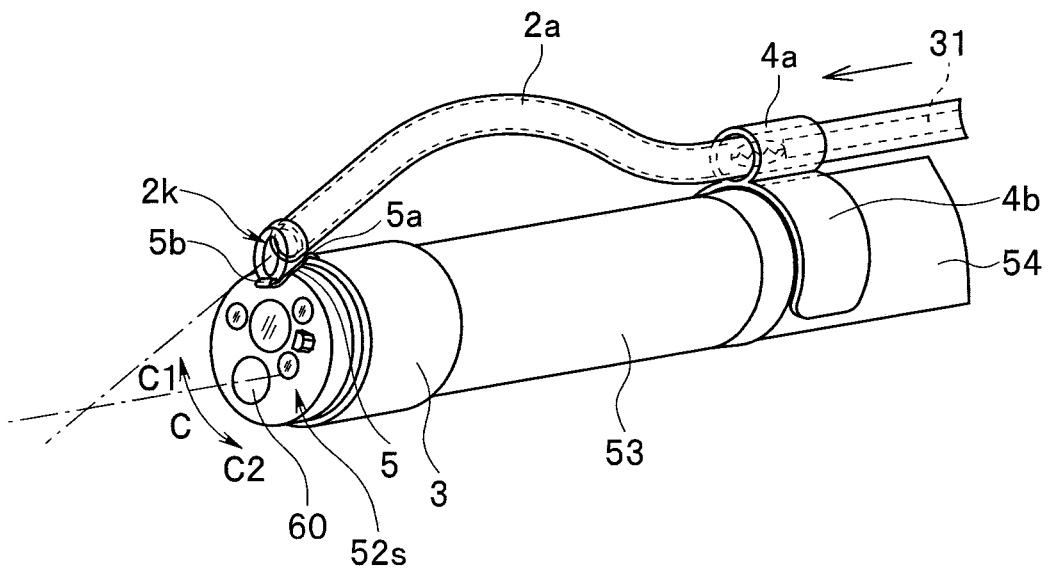
FIG. 13 is a partial perspective view illustrating a state in which the external channel including a grasping tool is moved in the external channel in FIG. 12 ahead of the position of the external channel in FIG. 12.

As illustrated in FIG. 12 and FIG. 13, as in the case of FIG. 11, when the entire external channel is made of a flexible identical member, a treatment instrument such as the grasping tool 31 is inserted into the external channel 2 close to the sliding portion 4a as illustrated in FIG. 12, and the hardness of the other region 2b is increased using the grasping tool 31, by pushing the external channel 2 forward, it may be possible to cause the distal end side region 2a to be deformed as in the case of the aforementioned embodiment as illustrated in FIG. 13.

When the distal end side region 2a is deformed and only the treatment instrument such as the grasping tool 31 is pushed forward and made to protrude from the distal end opening 2k as illustrated in FIG. 13, effects similar to the effects of the aforementioned embodiment can be obtained.

Note that to allow the operator to recognize the distal end position of the treatment instrument such as the grasping tool 31 before deforming the distal end side region 2a, that is, to allow the treatment instrument to be positioned accurately at the other region 2b, the external channel 2 may have such a configuration that the distal end side region 2a and the other region 2b are subjected to processes to have different inner circumferential surface sliding resistances or a protrusion is provided to generate click sensing as the treatment instrument passes through a boundary between the distal end side region 2a and the other region 2b on the inner circumferential surface of the external channel 2.

Figure 14:
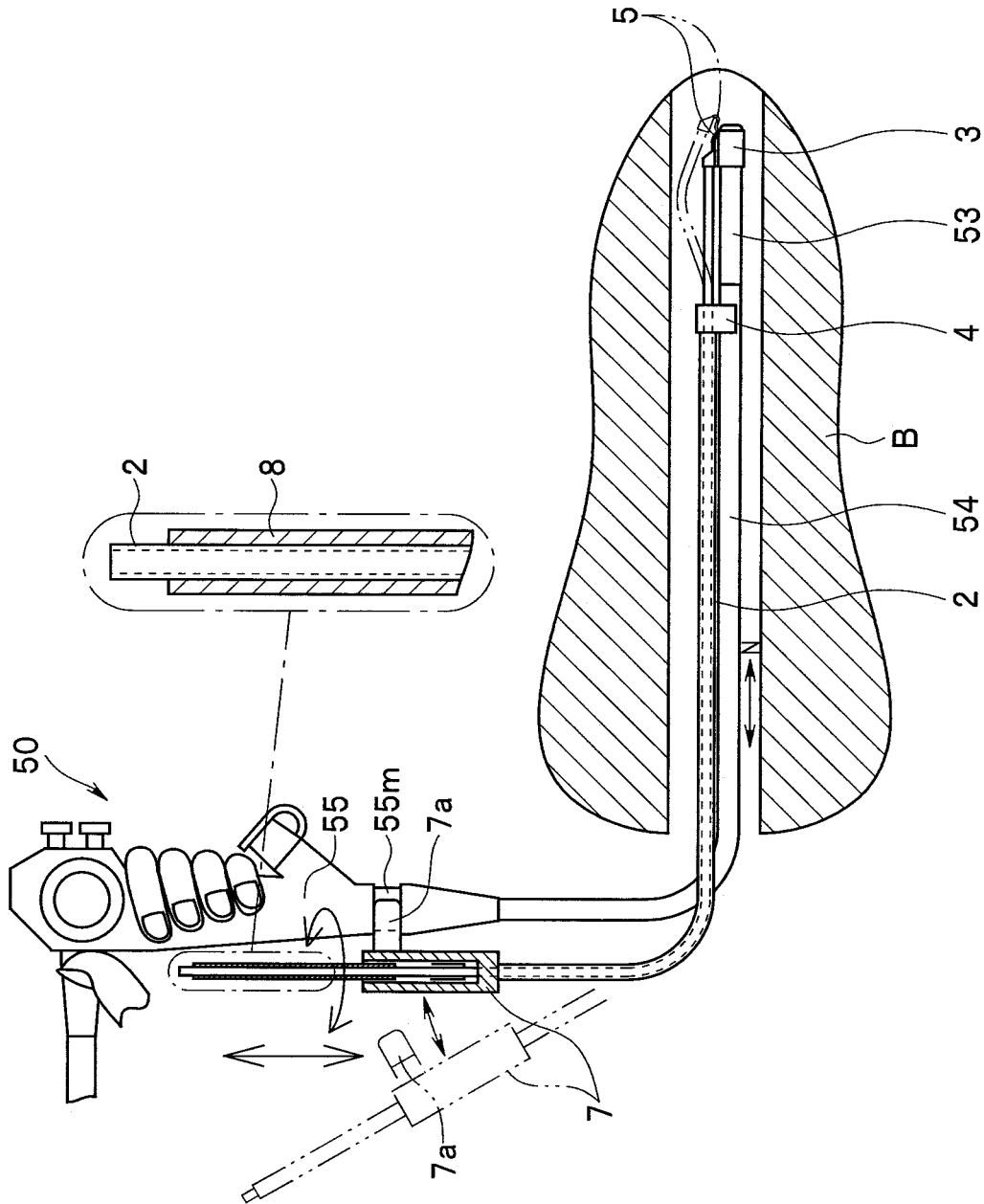
FIG. 14 is a diagram illustrating a modification in which the proximal end side of the external channel in FIG. 1 is configured to be attachable/detachable to/from the endoscope operation portion.

Hereinafter, a further modification will be illustrated using FIG. 14. FIG. 14 is a diagram illustrating a modification in which the proximal end side of the external channel in FIG. 1 is configured to be attachable/detachable to/from the endoscope operation portion.

As illustrated in FIG. 14, a configuration may be adopted in which a channel mounting member 7 is provided on the proximal end side of the external channel 2 and a mounting portion 7a for the channel mounting member 7 is attachable/detachable to/from a groove 55n provided in an operation portion 55.

Furthermore, a pipe-shaped grasping member 8 is fixed with adhesive to an outer circumference on the proximal end side of the external channel 2 and the grasping member 8 may be loosely fitted in the channel mounting member 7 in a movable manner.

According to such a configuration, with the channel mounting member 7 attached to the operation portion 55, the operator can perform an advancing/retreating operation or a twisting operation on the external channel 2 in the channel mounting member 7 while holding the grasping member 8.

Note that the rest of the configuration and effects are the same as the configuration and the effects of the aforementioned embodiment.

Figure 15:
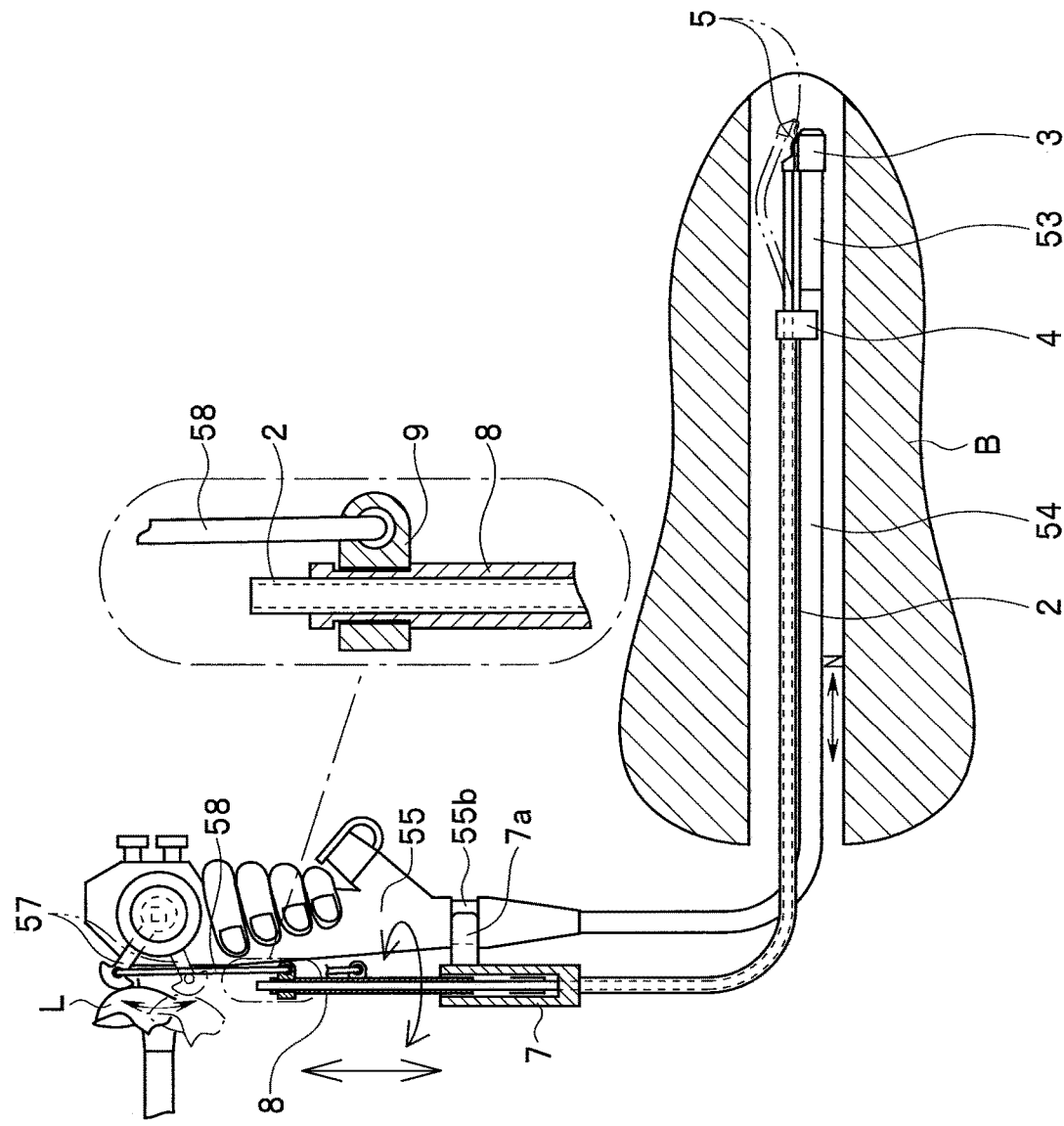
FIG. 15 is a diagram illustrating a configuration of a modification in which an advancing/retreating operation of the external channel in FIG. 14 is performed by a knob provided for the operation portion.

Furthermore, a configuration of the external channel proximal end side of a further modification will be illustrated hereinafter using FIG. 15. FIG. 15 is a diagram illustrating a configuration of a modification in which an advancing/retreating operation of the external channel in FIG. 14 is performed by a knob provided at the operation portion.

As illustrated in FIG. 15, the operation portion 55 may be provided with a turnable knob 57, a turning member 9 may be turnably fitted on the outer circumference at the proximal end of the grasping member 8, and a link member 58, one end of which is connected to the knob 57 and the other end of which is turnably connected to the turning member 9 may be provided, so as to perform an advancing/retreating operation on the external channel 2 via the link member 58, the turning member 9 and the grasping member 8 along with a turning operation of the knob 57.

Note that the twisting operation of the external channel 2 in this case is performed as a twisting operation carried out by the operator holding the grasping member 8 in the channel mounting member 7 as in the case of FIG. 14.

The rest of the configuration and effects are the same as the aforementioned configuration and effects illustrated in FIG. 14.

Figure 16:
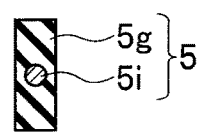
FIG. 16 is a cross-sectional view illustrating a specific example where the connection member in FIG. 1 is difficult to extend or contract in the longitudinal direction.

A further modification will be illustrated hereinafter using FIG. 16 to FIG. 18. FIG. 16 is a cross-sectional view illustrating a specific example where the connection member in FIG. 1 is difficult to extend or contract in the longitudinal direction, FIG. 17 is a cross-sectional view illustrating another specific example where the connection member in FIG. 1 is difficult to extend or contract in the longitudinal direction and FIG. 18 is a cross-sectional view illustrating a further specific example where the connection member in FIG. 1 is difficult to extend or contract in the longitudinal direction.

It has been shown in the aforementioned embodiment that the connection member 5 has a configuration characteristic that it is harder to deform (extend or contract) in the longitudinal direction N than in a direction crossing the longitudinal direction N.

As a specific example for realizing such a configuration, when the connection member 5 is made of rubber or the like, as illustrated in FIG. 16, a flexible and less extendable core member 5i may be provided in the longitudinal direction N inside rubber 5g that constitutes the connection member 5.

Figure 17:
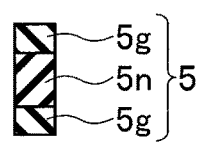
FIG. 17 is a cross-sectional view illustrating another specific example where the connection member in FIG. 1 is difficult to extend or contract in the longitudinal direction.
Figure 18:
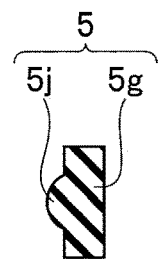
FIG. 18 is a cross-sectional view illustrating a further specific example where the connection member in FIG. 1 is difficult to extend or contract in the longitudinal direction.

On the other hand, as illustrated in FIG. 17, harder and less extendable rubber 5n than the rubber 5g may be provided in the longitudinal direction N inside the rubber 5g.

Furthermore, as illustrated in FIG. 18, a thick portion 5j may be provided in part of the rubber 5g in the longitudinal direction N.

According to the configurations illustrated in FIG. 16 to FIG. 18, in addition to the aforementioned effects of the present embodiment, it is possible to prevent unintentional extension and contraction in the longitudinal direction N caused by insertion and removal of the treatment instrument, allow some movement in a direction crossing the longitudinal direction N (e.g., direction inclined with respect to the longitudinal axis) and adjust the direction of the external channel 2.

Second Embodiment

Figure 19:
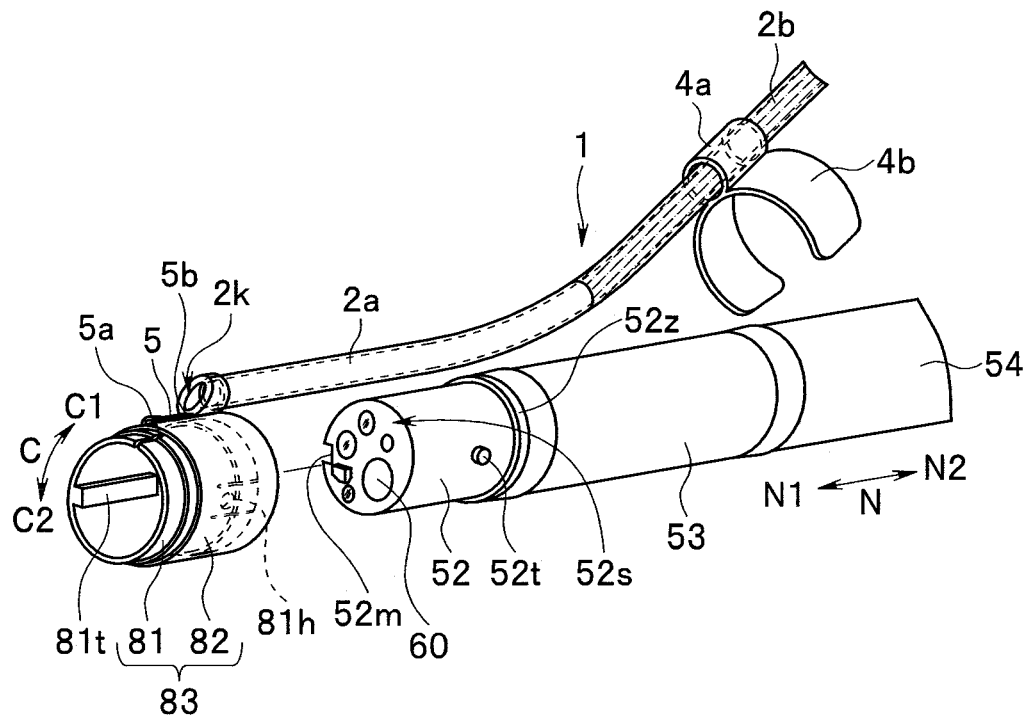
FIG. 19 is a partial perspective view illustrating a state in which a channel unit for an endoscope of a second embodiment is attached to the distal end side of the insertion portion of the endoscope.
Figure 20:
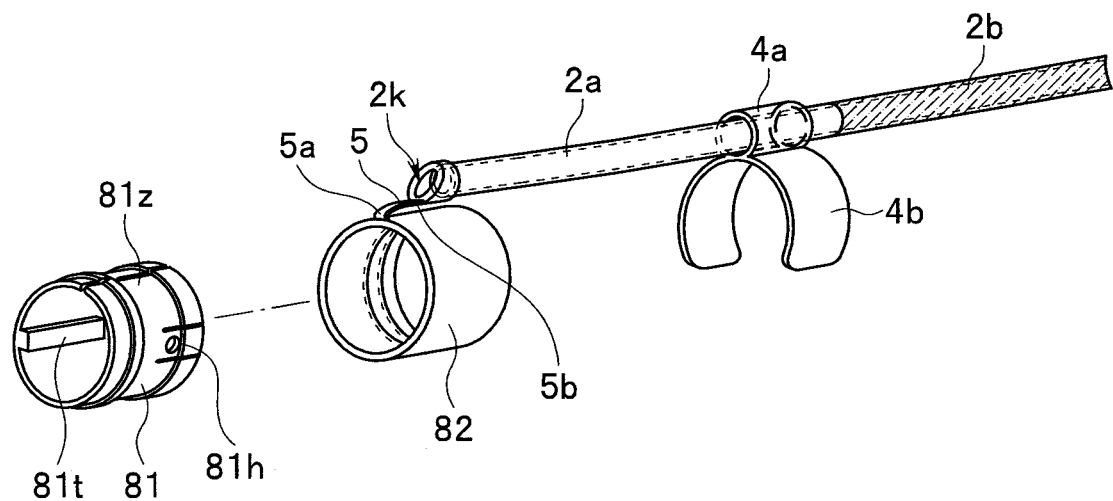
FIG. 20 is a partially exploded perspective view when a first cover is detached from the channel unit for an endoscope in FIG. 19.

FIG. 19 is a partial perspective view illustrating a state in which a channel unit for an endoscope of the present embodiment is attached to the distal end side of the insertion portion of the endoscope and FIG. 20 is a partially exploded perspective view when a first cover is detached from the channel unit for an endoscope in FIG. 19.

A configuration of the channel unit for an endoscope of the second embodiment is different from the aforementioned configuration of the channel unit for an endoscope of the first embodiment illustrated in FIG. 1 to FIG. 18 in that the mounting member is composed of two cover members and the mounting member is provided with a position defining member that defines a fixing position with respect to the distal end portion of the insertion portion of the endoscope.

Thus, only these differences will be described and components similar to the components of the first embodiment are assigned the same reference numerals and description of the components will be omitted.

It has been shown in the aforementioned first embodiment that the mounting member 3 of the channel unit 1 for an endoscope is fixed to the outer circumference of the distal end portion 52 of the insertion portion 51 by a frictional force.

However, with the frictional force alone, there is a possibility that the mounting member 3 may drop out of the distal end portion 52, and moreover, it is difficult to determine a fixing position of the distal end portion 52 in the circumferential direction C and thus perform mounting and fixing operations.

Thus, before inserting the insertion portion 51 to which the channel unit 1 for endoscope is attached into the subject B, it is necessary to cause the treatment instrument to protrude from the distal end opening 2k of the external channel 2 and adjust the position of the mounting member 3 in the circumferential direction C with respect to the distal end portion 52 while checking a protruding direction of the treatment instrument on a monitor.

Thus, in the present embodiment, a mounting member 83 includes a first cover 81 and a second cover 82 as illustrated in FIG. 19 and FIG. 20.

The first cover 81 is made of a rigid member such as resin, formed into a cylindrical shape and constitutes a region to be fixed to an outer circumference of the distal end portion 52.

On an inner circumferential surface of the first cover 81, a slide convex portion 81*t* is formed, which is position defining member to define a fixing position of the mounting member 83 in the circumferential direction C with respect to the distal end portion 52 in the longitudinal direction N.

Furthermore, in a fragile portion 81*z* formed on an outer circumference of the first cover 81, a through hole 81*h* is formed, which communicates with the inside and outside of the first cover 81 and which serves as a position defining member to define a fixing portion of the mounting member 83 in the circumferential direction C and the longitudinal direction N with respect to the distal end portion 52.

Note that the fragile portion 81*z* is formed to be thinner than the rest of the first cover 81 and is provided with a plurality of slits extending to the proximal end of the first cover 81 in the longitudinal direction N at a set interval in the circumferential direction C. In this way, the fragile portion 81*z* makes it easier to deform the proximal end side region of the first cover 81 to thereby make it easier to attach/detach the first cover 81 to/from the distal end portion 52.

The second cover 82 is made of an elastic member such as rubber and formed into a cylindrical shape, and the distal end side fixing portion 5*a* of the connection member 5 is connected to a distal end of the second cover 82.

The second cover 82 covers a region of the outer circumference of the first cover 81 that covers the through hole 81*h* and the fragile portion 81*z*.

Furthermore, when the mounting member 83 is fixed to the outer circumference of the distal end portion 52, a proximal end side region of the second cover 82 is closely fitted into the insulating ring 52*z* that engages with the outer circumference of the proximal end of the distal end portion 52 to thereby secure water tightness of the mounting member 83 and also fix the mounting member 83 to the outer circumference of the distal end portion 52 by a frictional force.

Note that when the mounting member 83 is fixed to the outer circumference of the distal end portion 52, a tight contact position of the second cover 82 with respect to the insulating ring 52*z* is offset in the longitudinal direction N from a position of the distal end side fixing portion 5*a* of the connection member 5 with respect to the second cover 82.

In this way, as shown in the aforementioned first embodiment, even if the distal end side region 2*a* of the external channel 2 is deformed, force is difficult to apply to the aforementioned tight contact position, which does not affect the tight contact state. Water tightness can therefore be fully ensured.

Furthermore, as illustrated in FIG. 19, a slide concave portion 52*m* in the longitudinal direction N is formed on the outer circumferential surface of the distal end portion 52 at a predetermined position of the circumferential direction C.

When the mounting member 83 is fixed to the distal end portion 52, the slide convex portion 81*t* is fitted into the slide concave portion 52*m* in the longitudinal direction N.

A locking pin 52*t* is provided upright on the proximal end side of the outer circumferential surface of the distal end portion 52. When the mounting member 83 is fixed to the distal end portion 52, the locking pin 52*t* is fitted into the through hole 81*h*.

Note that when the mounting member 83 is removed from the outer circumference of the distal end portion 52, the locking pin 52*t* is removed from the through hole 81*h* by the operator deforming and breaking the fragile portion 81*z*.

Note that the rest of the configuration is the same as the aforementioned configuration of the first embodiment.

According to such a configuration, when the mounting member 83 is fixed to the distal end portion 52, by only fitting the slide convex portion 82*t* into the slide concave portion 52*m* and fitting the locking pin 52*t* into the through hole 81*h*, it is possible to easily position the mounting member 83 with respect to the distal end portion 52 in the circumferential direction C and the longitudinal direction N.

Not only the frictional force of the second cover 82 but also the fitting of the locking pin 52*t* into the through hole 81*h* makes it less likely for the mounting member 83 to drop out of the outer circumference of the distal end portion 52.

Note that other effects are the same as the aforementioned effects of the first embodiment.

The aforementioned configuration of the present embodiment is also applicable to known side view type endoscopes. Hereinafter, configurations applied to the side view type endoscopes will be illustrated using FIG. 21 to FIG. 24.

Figure 21:
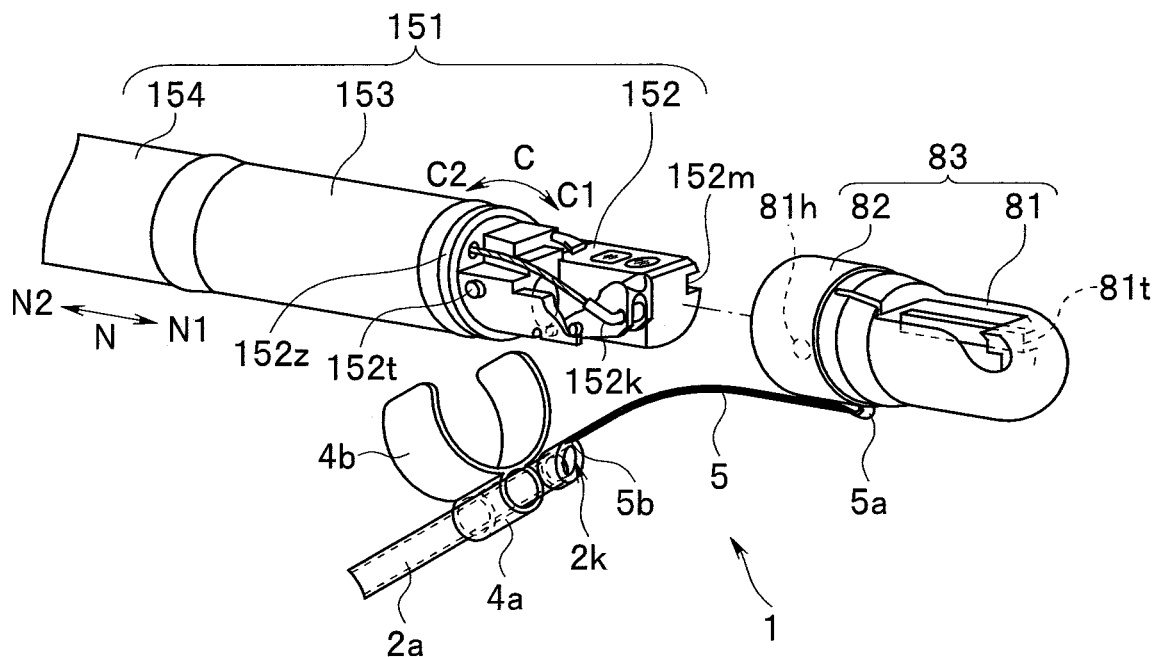
FIG. 21 is a partial perspective view illustrating the channel unit for an endoscope of the second embodiment together with the distal end side of the insertion portion of a side view type endoscope.
Figure 22:
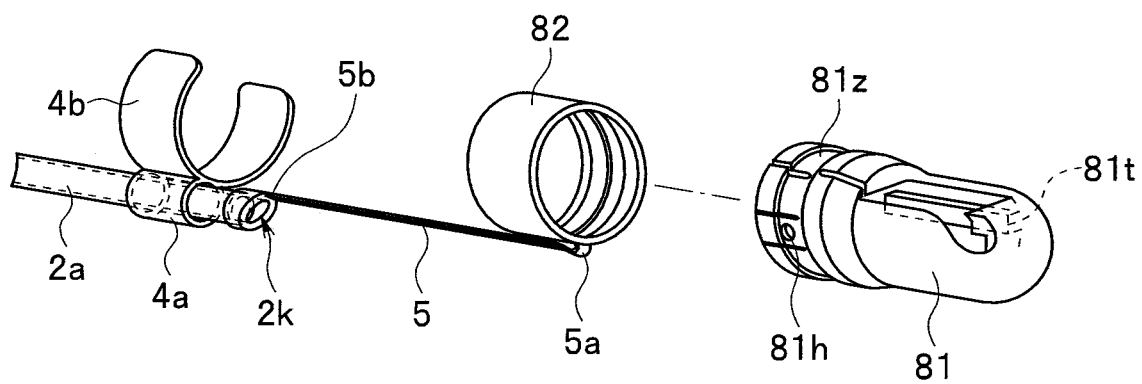
FIG. 22 is a partially exploded perspective view of the channel unit for an endoscope in FIG. 21 from which the first cover is detached.

FIG. 21 is a partial perspective view illustrating the channel unit for an endoscope of the present embodiment together with the distal end side of the insertion portion of a side view type endoscope and FIG. 22 is a partially exploded perspective view of the channel unit for an endoscope in FIG. 21 from which the first cover is detached.

Figure 23:
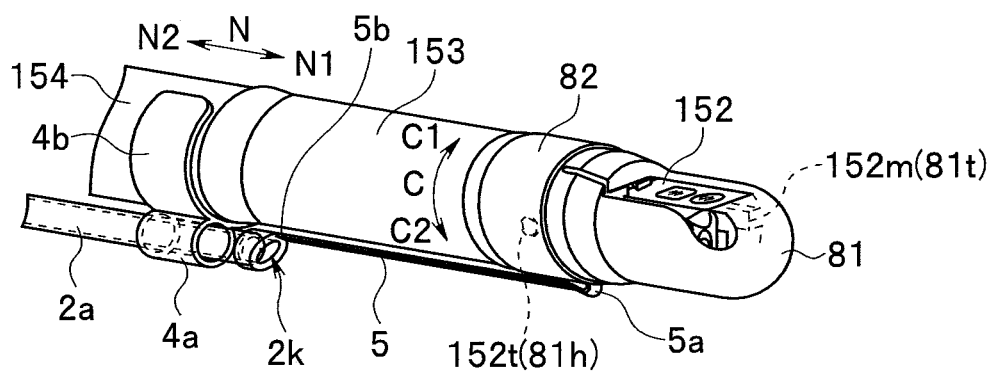
FIG. 23 is a partial perspective view illustrating a state in which the channel unit for an endoscope in FIG. 21 is attached to the distal end side of the insertion portion of the side view type endoscope.
Figure 24:
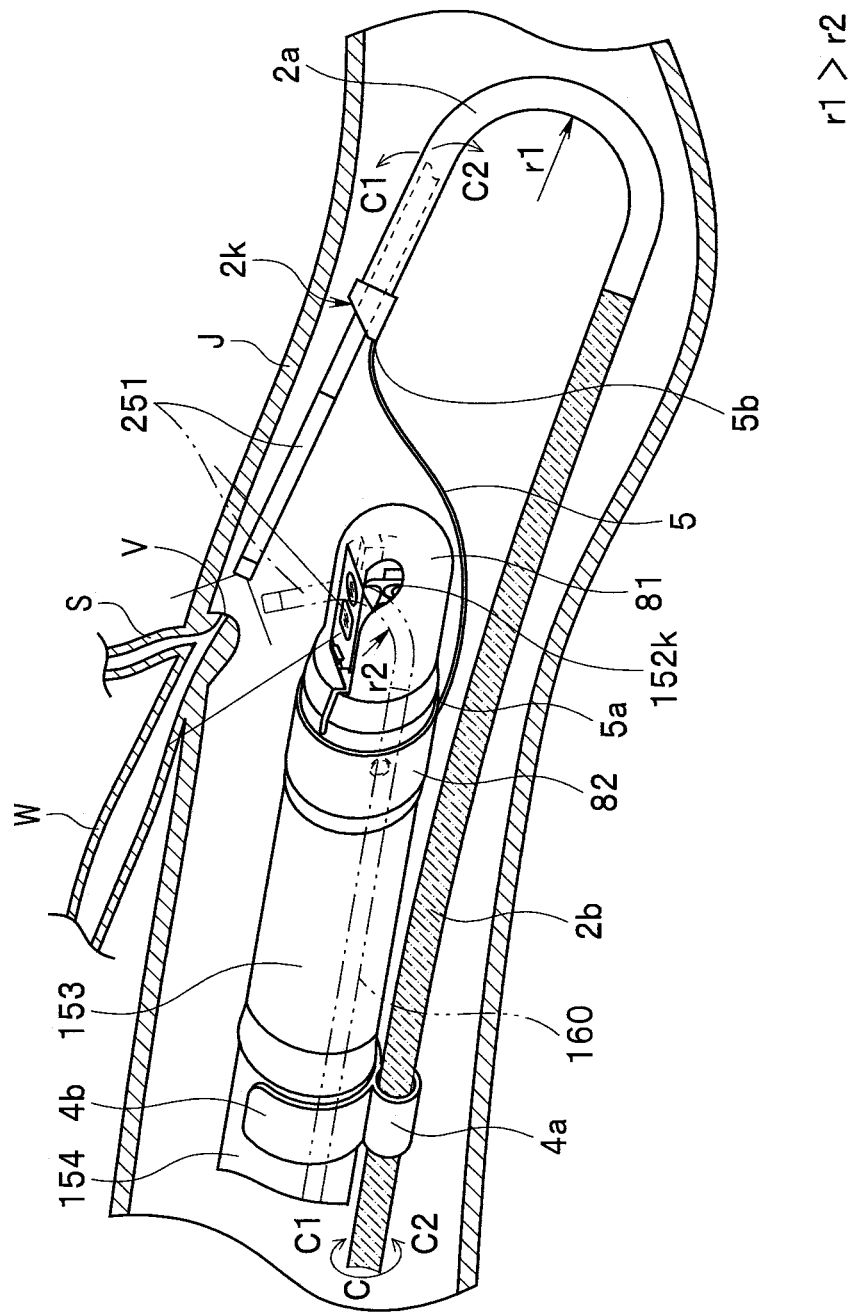
FIG. 24 is a diagram illustrating a state in which the insertion portion of the endoscope to which the channel unit for an endoscope in FIG. 23 is attached is inserted close to the duodenal papilla and another endoscope protruding from the distal end opening of the external channel is caused to face the papilla.

FIG. 23 is a partial perspective view illustrating a state in which the channel unit for an endoscope in FIG. 21 is attached to the distal end side of the insertion portion of the side view type endoscope and FIG. 24 is a diagram illustrating a state in which the insertion portion of the endoscope to which the channel unit for an endoscope in FIG. 23 is attached is inserted close to the duodenal papilla and another endoscope protruding from the distal end opening of the external channel is caused to face the papilla.

As illustrated in FIG. 21 to FIG. 23, the aforementioned channel unit 1 for an endoscope of the present embodiment is attached to the distal end side of an insertion portion 151 of a side view type endoscope.

The insertion portion 151 of the side view type endoscope includes a distal end portion 152, a bending portion 153 and a flexible tube portion 154, and an illumination lens, an objective lens and a fluid supply nozzle or the like are provided on a cutout surface formed by cutting out part of the outer circumference of the distal end portion 152, and in addition, a known treatment instrument raising base 152$k$ is provided at the distal end portion 152.

As in the case of the aforementioned embodiment, as illustrated in FIG. 21, a slide concave portion 152$m$ is formed in the longitudinal direction N at a predetermined position in the circumferential direction C on the outer circumferential surface of the distal end portion 152.

As illustrated in FIG. 23, when the mounting member 83 is inserted into the distal end portion 152, the slide convex portion 81$t$ is fitted into the slide concave portion 152$m$ in the longitudinal direction N.

A locking pin 152$t$ is provided upright on the proximal end side of the outer circumferential surface of the distal end portion 152. As illustrated in FIG. 23, the locking pin 152$t$ is fitted into the through hole 81$h$ when the mounting member 83 is inserted into the distal end portion 152.

Note that when the mounting member 83 is removed from the outer circumference of the distal end portion 152, the locking pin 152$t$ is removed from the through hole 81$h$ by the operator deforming and breaking the fragile portion 81$z$.

When the mounting member 83 covers the outer circumference of the distal end portion 152, the proximal end side region of the second cover 82 tightly engages with the insulating ring 152$z$ fitted into the outer circumference of the proximal end of the distal end portion 152 to thereby ensure water tightness of the mounting member 83 and fix the mounting member 83 to the outer circumference of the distal end portion 152 by a frictional force.

Furthermore, the locking portion 4$b$ of the locking member 4 is attached to the outer circumferential surface on the distal end side of the flexible tube portion 154.

Note that the rest of the configuration is the same as the aforementioned configuration of the present embodiment.

Even when applied to such a side view type endoscope, the channel unit for an endoscope of the present embodiment can obtain effects similar to the effects obtained by the aforementioned embodiment.

Furthermore, as shown in the aforementioned first embodiment, when the connection member 5 is formed to be long, as illustrated in FIG. 24, the insertion portion 151 to which the channel unit 1 for an endoscope is attached is orally inserted into the duodenum J and when the papilla V is observed using an objective lens provided at the distal end portion 152, if the external channel 2 is pushed forward, the distal end side region 2$a$ is deformed substantially 180° in the duodenum J to allow the distal end opening 2$k$ to face the papilla.

Therefore, as shown by a two-dot dashed line in FIG. 24, an insertion portion 251 of the other endoscope has been conventionally inserted into an insertion channel 160 of the side view type endoscope and the insertion portion 251 has been inserted into the papilla V, the bile duct W or the pancreatic duct S using the treatment instrument raising base 152$k$. However, there have been problems that a bending portion of the insertion portion 251 is easy to break when the insertion portion 251 passes through the treatment instrument raising base 152$k$ or since a radius of curvature r2 at the time of passing is small, the bending portion of the bent insertion portion 251 is easy to break.

However, in the configuration in which the insertion portion 251 is caused to protrude from the distal end opening 2$k$ of the external channel 2 and is inserted into the papilla V, a radius of curvature r1 of the deformed distal end side region 2$a$ is larger than a radius of curvature r2 (r1>r2), and so the insertion portion 251 bent when the insertion portion 251 passes through the distal end side region 2$a$ is not easy to break.

Moreover, since it never passes through the treatment instrument raising base 251$k$, the insertion portion 251 is less likely to break.

Furthermore, since it is easy to cause the distal end opening 2$k$ to face the papilla V, it is particularly easier to insert the insertion portion 251 into the bile duct W via the papilla V.

Even when the insertion portion 151 is moved somewhat, since the insertion portion 251 less follows the connection member 5 and the external channel 2, it is easier to insert the insertion portion 251 into the papilla V.

Note that when the insertion portion 251 made to protrude from the distal end opening 2$k$ is inserted into the papilla V, an auxiliary operation such as supporting the insertion portion 251 may be performed using a treatment instrument inserted into the insertion channel 160, a direction of which is changed by the treatment instrument raising base 152$k$.

It goes without saying that the item to be inserted into the external channel 2 is not limited to the insertion portion 251 of the endoscope and may be a treatment instrument as well.

Figure 25:
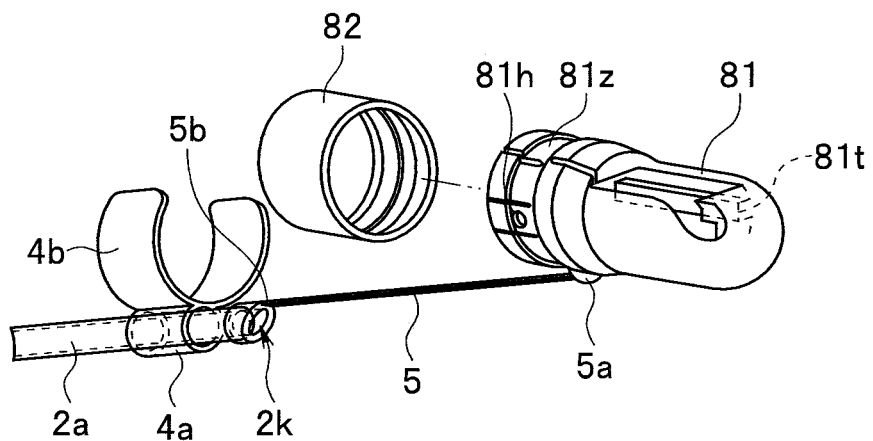
FIG. 25 is a partial perspective view illustrating a modification in which the distal end side fixing portion of the connection member in FIG. 22 is connected to the first cover.

Note that a modification will be illustrated using FIG. 25 hereinafter. FIG. 25 is a partial perspective view illustrating a modification in which the distal end side fixing portion of the connection member in FIG. 22 is connected to the first cover.

As illustrated in FIG. 25, even when the distal end side fixing portion 5$a$ of the connection member 5 is fixed to the first cover 81, it is possible to obtain effects similar to the effects of the aforementioned embodiment.

Figure 26:
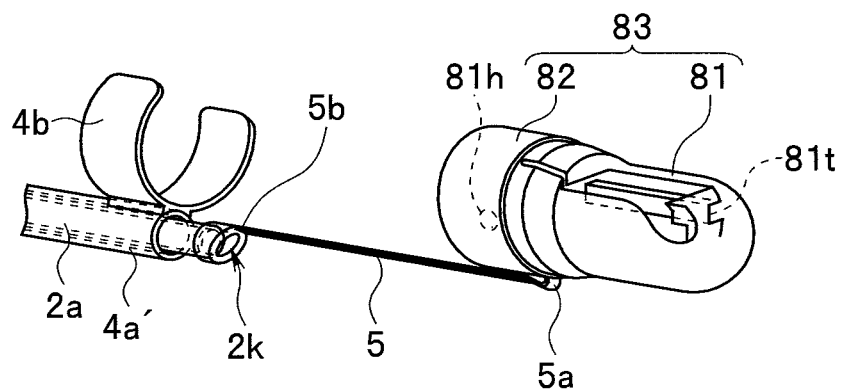
FIG. 26 is a partial perspective view illustrating a modification in which a sliding portion of the locking member in FIG. 21 is formed up to a proximal end of the external channel.

Another modification will be illustrated using FIG. 26. FIG. 26 is a partial perspective view illustrating a modification in which a sliding portion of the locking member in FIG. 21 is formed up to a proximal end of the external channel.

As illustrated in FIG. 26, the entire external channel 2 may be made of a flexible identical member and the outer circumference of the other region 2b except the distal end side region 2a may be covered with the rigid sliding portion 4a' of the locking member 4.

Furthermore, apart from the sliding portion 4a, the outer circumference of the other region 2b may also be covered with a guide tube.

With such a configuration, when the external channel 2 is pushed forward, the flexible distal end side region 2a, which is not covered with the sliding portion 4a' or the guide tube, is deformed as in the case of the aforementioned first embodiment, and so effects similar to the aforementioned effects of the first and second embodiments can be obtained.

Moreover, since it is not necessary to make the external channel 2 differently in hardness between the distal end side region 2a and the other region 2b, it is possible to reduce manufacturing cost.

Moreover, in the pushing operation or pulling operation of the external channel 2, since the external channel 2 moves back and forth in the longitudinal direction N, the external channel 2 may slide to directly contact the body wall of the subject B.

However, according to the present configuration, since the outer circumference of the other region 2b is covered with the sliding portion 4a' or the guide tube, it is possible to prevent the external channel 2 from contacting the body wall of the subject B.

According to the above-described embodiments, it is possible to provide a channel unit for an endoscope capable of adjusting the distal end opening of the conduit to a desired position or angle in a variable manner without changing the observation direction of the endoscope and an endoscope equipped with such a channel unit.

When carrying out endoscopic treatment such as ESD (endoscopic submucosal dissection) or duodenal surgery, this makes it possible to adjust the position of a treatment instrument that protrudes from the external channel attached at an angle with respect to the endoscope insertion portion to a desired position or angle without moving the endoscope insertion portion, and so it is possible to obtain an effect of being able to easily and reliably hold and treat a region to be treated such as a lesion, and thus significantly improve performance of treatment under endoscope using, for example, a treatment instrument made to protrude from the distal end opening of the external channel of the endoscope.

It goes without saying that the aforementioned embodiments are applicable not only to the treatment instrument described in the aforementioned embodiments but also to cases where other various types of treatment instruments or endoscopes are used.

What is claimed is:

1. A channel unit for use with an endoscope, the channel unit comprising:
   an elongated conduit configured to extend in a longitudinal direction;
   a distal mount configured to be fixed to a distal end side of an insertion portion of the endoscope; and
   a flexible elongated connection member having a first end connected to the distal mount and a second end connected to a distal end of the conduit, the first end of the connection member and the second end of the connection member being separated from each other in the longitudinal direction such that the second end of the connection member is at least movable longitudinally relative to the distal mount, wherein
   the distal end of the counduit is at least movable longitudinally relative to the distal mount between a first state and a second state such that,
      in the first state, the second end of the connection member is proximal to a distal end of the distal mount; and
      in the second state, the second end of the connection member is distal to the distal end of the distal mount.

2. The channel unit according to claim 1, wherein the second end of the connection member is further movable in a circumferential direction of the distal mount in response to a rotation of the conduit around a longitudinal axis.

3. The channel unit according to claim 1, further comprising a proximal mount provided proximally relative to the distal mount, the proximal mount being configured to fix a portion of the conduit to an outer circumferential surface of the insertion portion such that the portion of the conduit slides distally and proximally relative to the insertion portion.

4. The channel unit according to claim 1, wherein a length in the longitudinal direction between the first end and the second end of the connection member is variable.

5. The channel unit according to claim 4, wherein the distal mount includes a hook for slidably connecting the first end of the connection member to the distal mount.

6. The channel unit according to claim 1, wherein the conduit comprises a distal opening,
   in the first state, the distal opening is oriented towards a first direction, and
   in the second state, the distal opening is oriented towards a second direction different from the first direction.

7. The channel unit according to claim 6, wherein in the second state, the distal opening tilts radially inward.

8. The channel unit according to claim 6, wherein the second direction is configured so that the distal opening is oriented more toward the distal mount than the first direction.

9. The channel unit according to claim 6, wherein the first direction is a distal direction and the second direction is a proximal direction.

10. The channel unit according to claim 1, wherein the distal mount, the connection member and the conduit are formed of a single unitary piece.

11. The channel unit according to claim 1, wherein the conduit comprises:
    a distal end side region; and
    a proximal end side region;
    wherein the distal end side region is more flexible than the proximal end side region.

12. The channel unit according to claim 1, further comprising:
    a rigid tube covering a proximal end side region of the conduit, and
    wherein the conduit is more flexible than the rigid tube.

13. The channel unit according to claim 1, wherein the distal mount comprises a protrusion configured to restrict rotation of the distal mount relative to of the insertion portion.

14. The channel unit according to claim 1, wherein the connection member is more flexible in the longitudinal direction than in a direction intersecting the longitudinal direction.

15. An endoscope system, the endoscope system comprising:
    the channel unit according to claim 1; and
    the endoscope comprising the insertion portion.

16. The endoscope according to claim 15, further comprising a proximal mount provided proximally relative to the distal mount, the proximal mount being configured to fix a portion of the conduit to the outer circumferential surface of the insertion portion such that the portion of the conduit slides distally and proximally relative to the insertion portion.

17. The channel unit according to claim 1, wherein a movable area of the second end has a radius that is same as a length of the connection member.

18. A channel unit for use with an endoscope, the channel unit comprising:
- an elongated conduit configured to extend in a longitudinal direction;
- a distal mount configured to be fixed to a distal end side of an insertion portion of the endoscope; and
- a flexible elongated connection member having a first end connected to a distal end portion of the conduit;
- wherein, the distal mount includes a hook;
- the connection member having a portion slidably engaged with the hook;
- the first end of the connection member and the portion of the connection member engaged with the hook being separated from each other in the longitudinal direction; and
- the connection member extends proximally from the hook to a second end of the connection member such that proximally pulling the second end of the connection member moves the distal end portion of the conduit at least longitudinally relative to the hook.

* * * * *